(12) United States Patent
Yang

(10) Patent No.: US 11,282,221 B1
(45) Date of Patent: Mar. 22, 2022

(54) IMAGE CONTOURING USING SPIKING NEURAL NETWORKS

(71) Applicant: VARIAN MEDICAL SYSTEMS, INC., Palo Alto, CA (US)

(72) Inventor: Wenlong Yang, Shanghai (CN)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 17/027,891

(22) Filed: Sep. 22, 2020

(51) Int. Cl.
G06K 9/00 (2006.01)
G06T 7/55 (2017.01)
G06T 7/00 (2017.01)

(52) U.S. Cl.
CPC .............. *G06T 7/55* (2017.01); *G06T 7/0012* (2013.01); *G06T 2207/10081* (2013.01); *G06T 2207/20081* (2013.01); *G06T 2207/20084* (2013.01)

(58) Field of Classification Search
CPC ...................... G06T 7/55; G06T 7/0012; G06T 2207/10081; G06T 2207/20081; G06T 2207/20084
USPC ......................................................... 382/131
See application file for complete search history.

(56) References Cited

U.S. PATENT DOCUMENTS

| | | | | |
|---|---|---|---|---|
| 2014/0122400 A1* | 5/2014 | Szatmary | ............... | G06N 3/088 706/15 |
| 2015/0278641 A1* | 10/2015 | Agrawal | ................ | G06N 3/049 382/157 |
| 2017/0236027 A1 | 8/2017 | Van Der Made et al. | | |
| 2017/0314930 A1* | 11/2017 | Monterroza | ......... | G06N 3/0454 |
| 2017/0337469 A1* | 11/2017 | Debes | .................... | G06N 3/088 |
| 2019/0042942 A1* | 2/2019 | Natroshvili | ............ | G06N 3/088 |
| 2019/0213472 A1* | 7/2019 | Park | ..................... | G06N 3/0635 |
| 2020/0218959 A1* | 7/2020 | Srinivasa | ............... | G06N 3/049 |
| 2020/0218977 A1* | 7/2020 | Paul | ...................... | G06N 3/049 |

OTHER PUBLICATIONS

Meftah, B., Lezoray, O. & Benyettou, A. Segmentation and Edge Detection Based on Spiking Neural Network Model. Neural Process Lett 32, 131-146 (2010). https://doi.org/10.1007/s11063-010-9149-6 (Year: 2010).*

(Continued)

*Primary Examiner* — Van D Huynh
(74) *Attorney, Agent, or Firm* — Foley & Lardner LLP

(57) ABSTRACT

Disclosed herein are methods and system for training artificial intelligence models configured to execute image segmentation techniques. The methods and system describe a server that receives a first image including a set of pixels depicting multiple objects. The server also receives a second image having a second set of pixels depicting the same set of objects. The server then analyzes the pixels from the first and second images. When a difference between at least one visual attribute of a pixel within the second image and a corresponding pixel within the first image satisfies a predetermined threshold, it will be encoded as spikes to send to the model, the model will be trained using supervised STDP rule by revising weights associated with the nodes within the AI model where the node corresponds to the pixels within the first and/or the second image.

20 Claims, 12 Drawing Sheets

(56) References Cited

OTHER PUBLICATIONS

Lin X., Wang X., Cui W. An Automatic Image Segmentation Algorithm Based on Spiking Neural Network Model. In: Huang DS., Bevilacqua V., Premaratne P. (eds) Intelligent Computing Theory. ICIC 2014. Lecture Notes in Computer Science, vol. 8588. Springer, Cham. https://doi.org/10.1007/978-3-319-09333 (Year: 2014).*

International Search Report and Written Opinion for PCT/US2021/051121 dated Jan. 28, 2022 (13 pages).

Kirkland et al., "SpikeSEG: Spiking Segmentation via STDP Saliency Mapping", International Joint Conference on Neural Networkds (IJCNN), IEEE, Jul. 2020, pp. 1-8, DOI: 10.1109/IJCNN48605.2020.9207075 (8 pages).

Ponulak et al., "Supervised Learning in Spiking Neural Networks with ReSuMe: Sequence Learning, Classification, and Spike Shifting", Neural Computation, vol. 22, No. 2, Jan. 2010, pp. 467-510, DOI: 10.1162/neco.2009.11-08-901 (44 pages).

\* cited by examiner

IMAGE CONTOURING USING SPIKING NEURAL NETWORKS

TECHNICAL FIELD

This application relates generally to generating, training, and operating artificial intelligence models to perform image recognition and automatic contouring.

BACKGROUND

Comparing a temporal series of medical images taken at different times during treatment can indicate whether a patient is positively responding to the prescribed treatment. For example, a medical professional may compare a temporal series of computerized tomography (CT) scans (e.g., CT scan imagery generated every week since the beginning of the treatment) of a patient's tumor taken before and throughout the patient's treatment plan. The medical professional may then compare the size of the tumor to gauge how well the patient has responded to his/her prescribed treatment.

Many medical professionals utilize artificial intelligence-enabled image recognition software solutions to analyze temporal series of images and to provide insights regarding the patient's treatment. Conventional image recognition software solutions typically use artificial intelligence (AI) image recognition techniques to identify the desired object within the temporal series of images. For instance, the temporal series of images may include various organs of the patient. Conventional software solutions may use AI image recognition techniques to segment/contour each image and to identify the organ/object to which the treatment is directed. After identifying the desired organ/object within each image, conventional software solutions can compare and analyze various attributes of the identified organ/object.

Some conventional software solutions use manual target contouring to identify the desired organ/object within each image. Furthermore, some conventional software solutions also use conventional AI training methods to train the AI model configured to identify/contour the desired object. Some conventional software solutions use neural network technologies, such as recurrent neural networks (RNN), deep learning techniques, and/or long short-term memory (LSTM) technology to contour and segment images.

FIG. 1A represents a conventional AI training method. As depicted, an AI system 100 uses conventional deep learning techniques for temporal image recognition tasks. The AI system 100 receives raw data (e.g., medical images) and extracts various features from each image. A deep learning neural network is subsequently trained using characterization of a temporal relationship of the extracted features. For instance, a medical professional may review the extracted features and provide the temporal characterization. The AI system 100 may train itself using the received data, such that when AI model receives a new image, the AI system 100 can automatically segment the new image.

However, conventional AI training methods have faced technical shortcomings. For instance, conventional deep learning neural network systems for temporal tasks require training of the system with a large number of reference images. This training method is both computationally intensive and costly. Furthermore, conventional AI training methods require a medical professional to analyze ground truth datasets (e.g., images of previous patients) in order to train the AI model used, which is costly and inevitably leads to a long training period.

SUMMARY

For the aforementioned reasons, there is a desire for an improved AI modeling/training technique that does not rely solely on receiving ground truth training data set from medical professionals. There is a desire for methods and systems to train artificial intelligence image recognition models with minimal human intervention (e.g., a medical professional revising the model). There is a desire to train AI models based on differences identified within the captured medical images. What is desired is an AI modeling/training technique that is more efficient and produces results that are more accurate without needing a large training dataset.

The methods and systems described herein address the above-described technical shortcomings by providing a training system that does not require a large number of ground truth training images and provides accurate results. The described AI training methods/systems allow a server to extract multiple images/frames from a media element (e.g., medical images of a patient), analyze pixels within each image, and only train an AI model based on visual attribute differences between the images. More specifically, the server can revise synaptic node weights associated with pixels with changing visual attributes, such as grayscale attributes. For instance, the server only trains the AI model when visual attributes of corresponding pixels satisfy a visual attribute threshold. Therefore, the disclosed AI training methods/systems address technical problems of conventional AI software solutions in two ways. First, the server only focuses its training on visual differences, which reduces the number of images and computing power needed to train the AI model. Second, because the server needs fewer images to train the AI model, the server can utilize a patient's own images for training purposes, which improves accuracy.

In an embodiment, a method comprises executing, by a computer, an artificial intelligence model utilizing a spiking neural network to segment one or more objects represented by a first set of pixels in a first three-dimensional image, the spiking neural network comprising a set of nodes corresponding to the first set of pixels, each node having a synaptic weight, wherein at least a first portion of nodes within the set of nodes represents input nodes corresponding to the first set of pixels and a second portion of the nodes within the set of nodes represents output nodes associated with a likelihood of each respective pixel corresponding to at least one object within the one or more objects; comparing, by the computer, a grayscale attribute of each pixel within the first set of pixels with a corresponding pixel within a second set of pixels of a second image of the one or more objects; iteratively training, by the computer using a supervised spiked-timing dependent plasticity method, the spiking neural network by: in response to a difference between grayscale attributes of a first pixel within the first set of pixels with a second pixel within the second set of pixels satisfying a predetermined threshold a node corresponding to the first pixel transmits a spike, and revising a corresponding synaptic weight associated with the first or the second pixel with each iteration; and upon receiving a third image, executing, by the computer, the artificial intelligence model utilizing a trained spiking neural network to segment the one or more objects in the third image.

In another embodiment, a server comprises a processor and a non-transitory computer-readable medium containing instructions that when executed by the processor causes the processor to perform operations comprising: execute an artificial intelligence model utilizing a spiking neural network to segment one or more objects represented by a first set of pixels in a first image, the spiking neural network comprising a set of nodes corresponding to the first set of pixels, each node having a synaptic weight, wherein at least a first portion of nodes within the set of nodes represents input nodes corresponding to the first set of pixels and a second portion of the nodes within the set of nodes corresponds to a likelihood of each respective pixel corresponding to at least one object within the one or more objects; compare a grayscale attribute of each pixel within the first set of pixels with a corresponding pixel within a second set of pixels of a second image of the one or more objects; iteratively train using a supervised spiked-timing dependent plasticity method, the spiking neural network by: in response to a difference between grayscale attributes of a first pixel within the first set of pixels with a second pixel within the second set of pixels satisfying a predetermined threshold a node corresponding to the first pixel transmits a spike having, and revising a corresponding synaptic weight associated with the first or the second pixel with each iteration; upon receiving a third image, execute the artificial intelligence model utilizing a trained spiking neural network to segment the one or more objects in the third image.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1A:
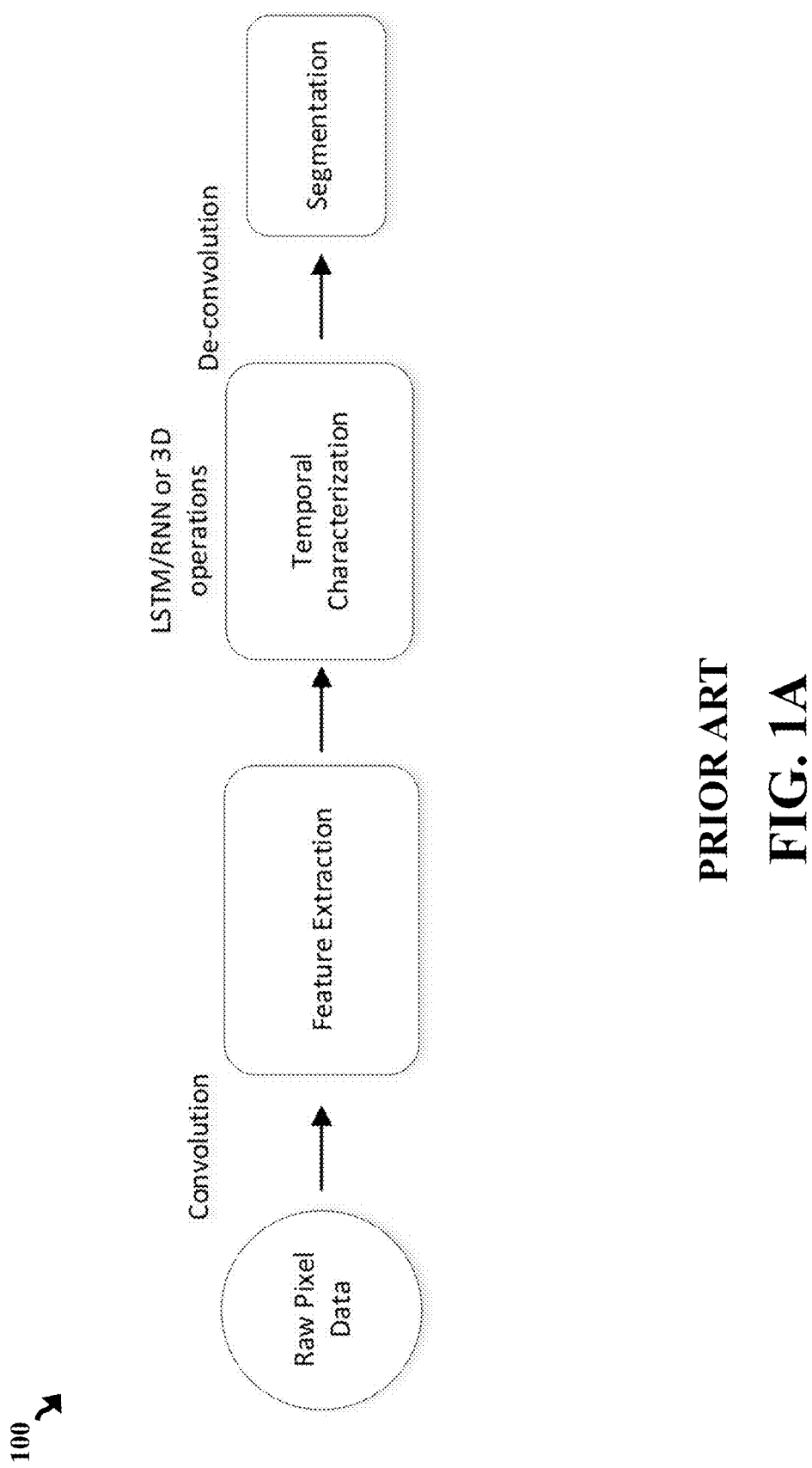
FIG. 1A illustrates a conventional method of training AI models, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Disclosed herein are methods and systems that address technical shortcomings associated with conventional AI-enabled image recognition software solutions. These methods and systems are described below. More specifically, FIG. 1B illustrates a non-limiting example of a computer environment in which one or more servers (e.g., the analytics server) can receive images, train AI models accordingly, and display results. The AI training methods described herein can be implemented using computing features described and illustrated in FIG. 1B.

FIG. 1B illustrates components of an AI training system 101. The AI training system 101 may include an analytics server 110a, system database 110b, user computing devices 120a-d (collectively user computing devices 120), electronic data sources 140a-e (collectively electronic data source 140), and an administrator computing device 150. The above-mentioned components may be connected to each other through a network 130. The examples of the network 130 may include, but are not limited to, private or public LAN, WLAN, MAN, WAN, and the Internet. The network 130 may include both wired and wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The training system 100 is not confined to the components described herein and may include additional or alternate components, not shown for brevity, which are to be considered within the scope of the embodiments described herein.

The analytics server 110a may generate and display an electronic platform configured to use various AI models to display the predicted results, such as the received medical images and segmentation/contouring results. The electronic platform may include graphical user interface (GUI) displayed on each user computing device 120 and/or the administrator computing device 150. An example of the electronic platform generated and hosted by the analytics server 110a may be a web-based application or a website configured to be displayed on different electronic devices, such as mobile devices, tablets, personal computer, and the like (e.g., user computing devices 120).

The analytics server 110a may host a website accessible to end-users, where the content presented via the various webpages may be controlled based upon each particular user's role or viewing permissions. The analytics server 110a may be any computing device comprising a processor and non-transitory machine-readable storage capable of executing the various tasks and processes described herein. Non-limiting examples of such computing devices may include workstation computers, laptop computers, server computers, laptop computers, and the like. While the system 100 includes a single analytics server 110a, in some configurations, the analytics server 110a may include any number of computing devices operating in a distributed computing environment.

The analytics server 110a may execute software applications configured to display the electronic platform (e.g., host a website), which may generate and serve various webpages to each user computing device 120. Different users operating the user computing devices 120 may use the website to view and/or interact with the predicted results.

In some implementations, the analytics server 110a may be configured to require user authentication based upon a set of user authorization credentials (e.g., username, password, biometrics, cryptographic certificate, and the like). In such implementations, the analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may also store data associated with each user operating one or more user computing devices 120. The analytics server 110a may use the data to weigh interaction while training various AI models accordingly. For instance, the analytics server 110a may indicate that a user is a medical professional whose inputs may be monitored and used to train the AI models described herein.

In some configurations, the analytics server 110a may generate and host webpages based upon a particular user's role within the AI training system 100 (e.g., administrator and/or employee). In such implementations, the user's role may be defined by data fields and input fields in user records stored in the system database 110b. The analytics server 110a may authenticate the user and may identify the user's role by executing an access directory protocol (e.g. LDAP). The analytics server 110a may generate webpage content that customized according to the user's role defined by the user record in the system database 110b.

In some embodiments, the analytics server 110a receives raw data (e.g., series of images) from a user (or retrieve from a data repository), analyzes the data, and displays the results (e.g., AI-based results) on the electronic platform. For instance, in a non-limiting example, a user operating the computing device 140a uploads a series of images of a CT scan or other medical images using the electronic platform. The analytics server 110a then uses various AI models (stored within the system database 110b) to analyze the uploaded image. The analytics serve 110a then displays the results (e.g., size and shape of a tumor) via the electronic platform on the administrator computing device and/or user computing devices 120.

User computing devices 120 may be any computing device comprising a processor and a non-transitory machine-readable storage medium capable of performing the various tasks and processes described herein. Non-limiting examples of a network node may be a workstation computer, laptop computer, tablet computer, and server computer. In operation, various users may use user-computing devices 120 to access the GUI operationally managed by the analytics server 110a.

The electronic data sources 140 may represent various electronic data sources that contain and/or can be used to retrieve the series of medical images. For instance, database 140b and third-party server 140c may represent data sources providing the corpus of data (e.g., images) needed for the analytics server 110a to train one or more AI models. The analytics server 110a may also retrieve the data directly from a medical scanner 140e and/or 140d (e.g., CT scan machine).

The administrator-computing device 150 may represent a computing device operated by a system administrator. The administrator-computing device 150 may be configured to display various analytic metrics where the system administrator can monitor the AI training, review feedback, and modify various thresholds/rules described herein.

In operation, the analytics server 110a may receive medical imaging from a medical imaging system (e.g., medical scanner 140d). As described herein, the analytics server 110a may train an Artificial intelligence model using extracted frames from the received medical image(s) and display the results onto the user computing devices 120 via the described platform.

Figure 1B:
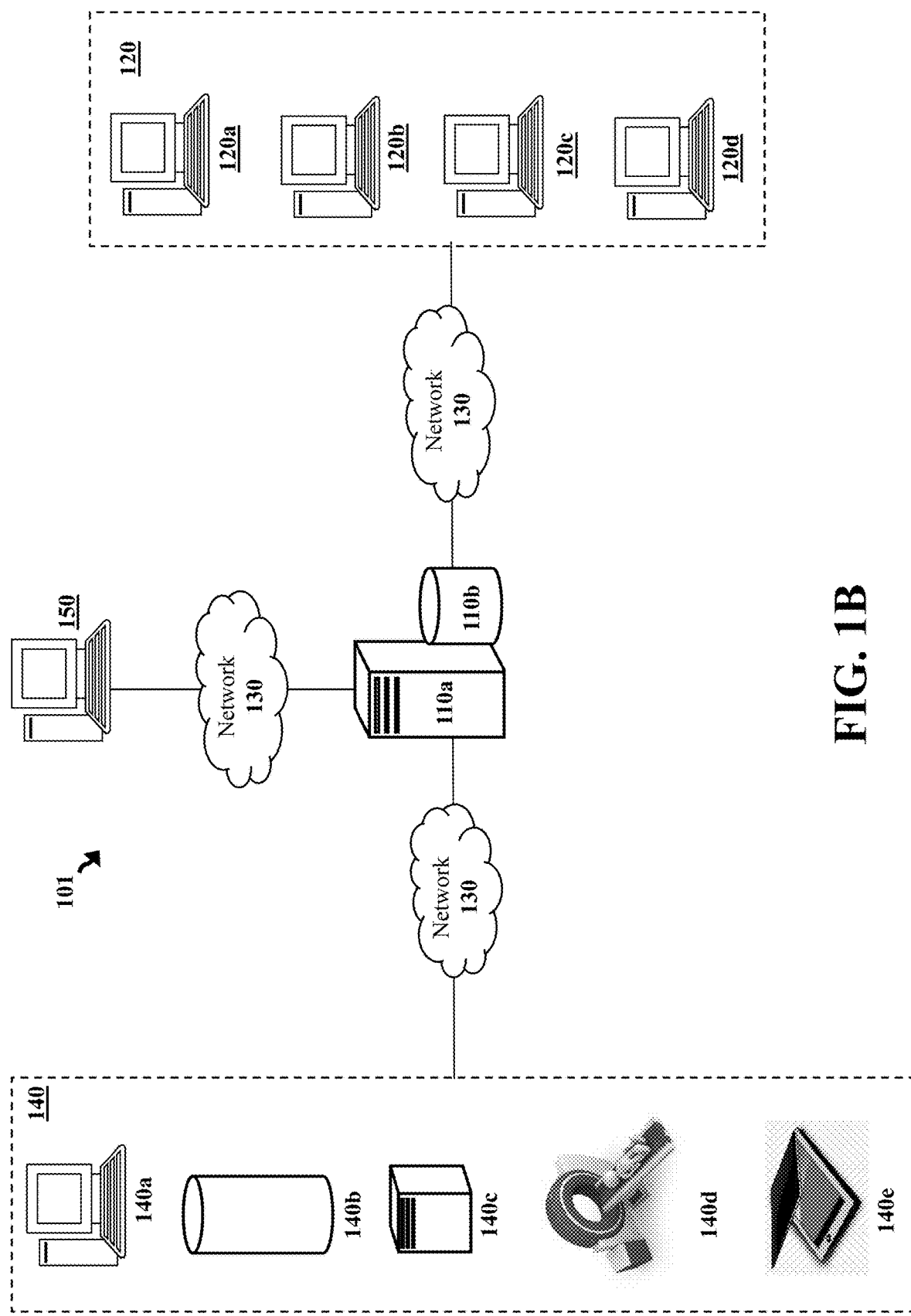
FIG. 1B illustrates components of an AI training system, according to an embodiment.
Figure 2:
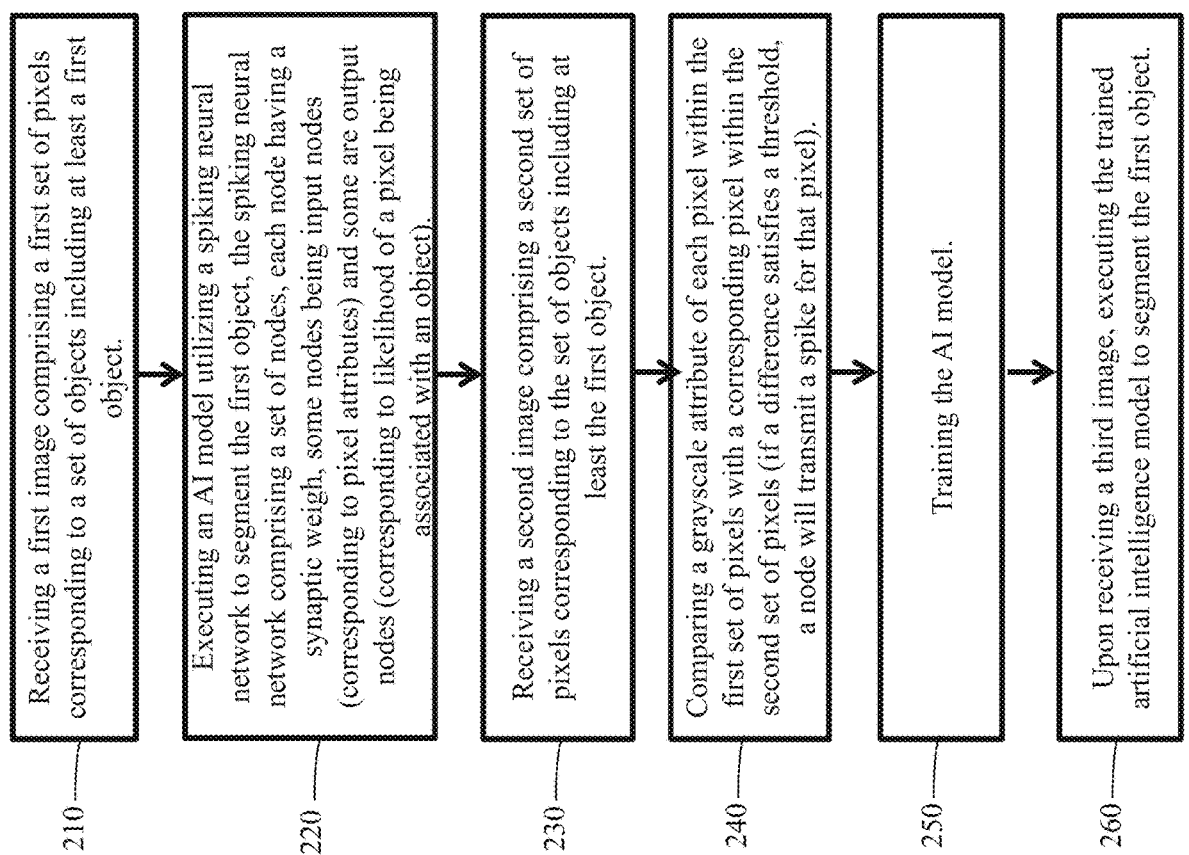
FIG. 2 illustrates a flow diagram of a process executed in an AI training system, according to an embodiment.

FIG. 2 illustrates a flow diagram of a process executed in an AI training system, according to an embodiment. The method 200 includes steps 210-260. However, other embodiments may include additional or alternative execution steps, or may omit one or more steps altogether. The method 200 is described as being executed by a server, similar to the analytics server described in FIG. 1B. However, one or more steps of method 200 may also be executed by any number of computing devices operating in the distributed computing system described in FIG. 1B. For instance, one or more user computing devices may locally perform part or all the steps described in FIG. 2.

Even though some aspects of the embodiments described herein are described within the context of clinical and health-care-specific imaging software, it is understood that methods and systems described herein apply to all AI models/training techniques and all AI-enabled image recognition software solutions. For instance, in other embodiments, the methods and systems described herein may be applied to an AI model that is configured to contour and segment any object within an image regardless of the object and the context of the image.

At step 210, the analytics server receives a first image comprising a first set of pixels corresponding to a set of objects including at least a first object. The analytics server may receive a first image depicting the desired object and/or other objects. The image may include multiple objects, one of which corresponds to the object to be identified and analyzed by the analytics server using the methods and systems described herein. In some embodiments, the first image may be an image within a series of medical images. Medical imaging is the technique and process of creating visual representations of the interior of a patient's body for clinical analysis and medical intervention, as well as visual representation of the function of some organs or tissues (physiology).

In an example, the first image may be a CT scan image of a patient where the CT scan image illustrates one or more objects such as one or more organs of the patient. The first image may also illustrate an object such as a tumor. The method 200, in conjunctions with the method 300 described in FIG. 300, illustrates how the analytics server can identify the tumor (e.g., segment and contour the pixels associated with the tumor). The analytics server can also train an AI model (e.g., spiking neural network), such that the trained AI model can receive a new set of images (e.g., CT scan belonging to a different patient) and automatically identify the new patient's tumor and/or contour the new patient's medical images. Another example of the image(s) received may include X-ray images.

Another example of the first image received may be a three/four-dimensional computed tomography (3D CT or 4D CT). A 3D CT is a type of CT scanning, which records multiple images over a predetermined time window. 4D CT allows playback of the scan as a video, so that physiological processes can be observed and internal movement can be tracked. Another example of the image(s) received may include images received via various fluoroscopy methods. Fluoroscopy is an imaging technique that uses X-rays to obtain real-time moving images of the interior of an object. In its primary application of medical imaging, a fluoroscope allows a physician to see the internal structure and function of a patient (e.g., pumping action of the heart or the motion of swallowing or breathing), such that these actions can be observed and analyzed. Fluoroscopy may be a similar technique to 4D CT. However it refers to the introduction of a time element to 2D planar radiography, rather than to 3D CT.

The first image (or any other image discussed herein) may include a set of pixels. A pixel may represent a smallest addressable element in the first image. In some embodiment, the analytics server may use various methods to identify each pixel within the set of pixels received. In some embodiments, a pixel may represent a predetermined segment of the first image (or any other image discussed herein). For instance, the analytics server may divide the image into a predetermined number of segments and/or into multiple segments having a predetermined size. A pixel, as used herein, is a small segment of an image that represents the amount of gray intensity (also referred to herein as grayscale attribute) to be displayed for that particular segment of the image. For most images, pixel values are integers that range from zero (black) to 255 (white).

At step 220, the analytics server may execute an artificial intelligence model utilizing a spiking neural network to segment one or more objects represented by a first set of pixels in a 3D image, the spiking neural network comprising a set of nodes corresponding to the first set of pixels, each node having a synaptic weight, wherein at least a first portion of nodes within the set of nodes represents input nodes corresponding to the first set of pixels and a second portion of the nodes within the set of nodes represents output nodes associated with a likelihood of each respective pixel corresponding to at least one object within the one or more objects. The analytics server may execute an AI model to identify different objects within the first image received. The AI model may use various artificial intelligence and image recognition techniques to identify various objects included in the first image (including the first object). The AI model may use various modeling techniques to ingest and analyze the first image, such as neural networks.

Non-limiting examples of neural networks include spiking neural networks (SNN). As used herein, SNN refers to a class of artificial neural networks that more closely mimic natural neural networks. In addition to neuronal and synaptic state, SNNs may incorporate the concept of time into their operating model. Unlike other multi-layer perceptron networks or other AI training methods, nodes in AI models utilizing SNN do not communicate with each propagation cycle, but rather communicate only when a specific value is reached (an intrinsic quality of the node reaches a specific value). When a specific value is reached (e.g., an attribute satisfies a predetermined threshold), one or more nodes generate a signal that travels to other nodes, which in turn, increase or decrease their potentials (e.g., related synaptic weights) in accordance with this signal.

One of SNNs distinguishing feature, when compared to conventional AI methodologies, is that nodes/neurons in these networks communicate amongst themselves using "spikes," as opposed to "real numbers" that nodes/neurons in deep-learning networks typically use for communication. While the class of SNNs are capable of carrying out the same functions as other neural networks, the communication using spikes (while using the methods and systems described herein) may provide an improved economy of information making these networks more power-efficient. Furthermore, the time-dependent interaction via spikes using method and systems described herein may turn these networks into dynamic systems capable of quickly adapting/training, which makes them more powerful than the conventional neural networks, such as CNNs or RNNs that operates on temporally static memory.

The methods and systems described herein are especially applicable to radiation oncology (e.g., using 4D CT imagery). Current 4D CT contouring techniques are typically performed offline, which has resulted in less accurate and/or results that are not timely produced. Some conventional systems use rigid or deformable methods to identify different objects (e.g., tumors) or use training from different patients, which also provides limited and/or partially accurate results. Using the methods and systems herein, a model may be trained using the patient's own imagery (in real time or in near real time), such that the image recognition applies to the patient himself/herself.

Some other conventional system use neural network technologies (e.g., recurrent neural network (RNN) or long short-term memory (LSTM)) to achieve temporal image recognition. However, these methodologies utilize complex structures that are difficult to train and to require more time to be trained. As expected, and especially in medical environments, conventional systems do not provide suitable results. Furthermore, configuring a conventional deep learning neural network system for temporal tasks has also not been ideal. These methods require training of the system with a large number of reference images, which is not practical.

In some configurations, the analytics server may use other AI modeling techniques. For instance, the analytics server may utilize a neural network, and the like. Therefore, the method and systems described herein apply to any AI modeling techniques.

The neural network may include three general types of nodes/neurons. Input nodes may correspond to nodes that identify one or more attributes of pixels within the images. Output nodes may correspond to nodes that identify a likelihood of a pixel being associated with an object. Inner nodes may correspond to any nodes, which are between input and output nodes and used for signal processing. Inner nodes are optional for the neural networks, while neural networks must have input nodes and output nodes.

At step 230, the analytics server may receive a second image comprising a second set of pixels corresponding to the set of objects including at least the first object. The analytics server may receive a second image. The second image may include a set of pixels corresponding to multiple images including the same or different objects within the first image. For instance, the second image may include the first object depicted in the first image. In some configurations, the second image may represent a temporal image of the same patient associated with the first image. For instance, the first image may be a CT scan of a patient depicting his/her abdominal area and may include multiple organs including the patient's tumor (e.g., the first object). The second image may also be a CT scan of the same patient at a different time (e.g., after receiving medical treatment including chemotherapy and/or radiotherapy or a second image taken during a respiratory cycle). The end user (e.g., physician) may compare the images to identify how the medical treatment has affected the patient's tumor (e.g., first object).

In some configurations, the analytics server may extract the first and/or the second image from a media element (e.g., gif, movie, or a series of images). For example, as described above, the analytics server may receive imagery produced using 4D CT scan performed on a patient. The 4D CT scan may correspond to multiple images produced within a predetermined amount of time. For instance, the 4D CT scan may include CT scan images of the patient breathing. More specifically the 4D CT scan image may start when the patient starts breathing and end when the patient has completed his breathing. Therefore, the 4D CT scan image may include a series of temporally consecutively produced images. When the analytics server receives the 4D CT scan image, the analytic server may extract multiple images based on their time sequence. For instance, the analytics server may extract a frame that correspond to a pre-determined time (e.g., one frame is extracted per 3 seconds or any other time indicated by the end user). Therefore, the second image may represent a neighbor phase (e.g., subsequent phase) of the 4D CT scan image.

At step 240, the analytics server may compare a grayscale attribute of each pixel within the first set of pixels with a corresponding pixel within a second set of pixels of a second image of the object. The analytics server may identify the set of pixels from the second image. As described above, the analytics server may use a variety of methods to extract the set of pixel of the second image. After extracting the set of pixels, the analytics server may compare visual attributed of the second image to the first image. For example, the analytics server may compare visual attribute of each pixel within the second image to a corresponding pixel of the first image. As described above, visual attribute may correspond to gray scale attribute of each pixel.

As will be described below, when a difference between attribute of a pixel (from the first image) and a corresponding pixel (from a second image) satisfies a difference, the node transmit a spike (e.g., communicating with other related nodes).

At step 250, the analytics server may train the AI model. The analytics server may train the AI model based on differences of the visual attributes of corresponding pixels of the first and second images satisfying a threshold, the analytics server may train the AI model accordingly. The analytics server may use a variety training method including but not limited to the method described in FIG. 3. For instance, the analytics server may compare a first pixel's (a pixel within the first image) visual attribute with a second pixel's (a corresponding pixel within the second image) visual attribute. If the difference between the corresponding pixels satisfy a threshold, the analytics server may train the AI model accordingly. The analytics server may use a supervised spiked-timing dependent plasticity (STDP) method as described in FIG. 3.

At step 260, the analytics server may, upon receiving a third image, execute the trained artificial intelligence model to identify the first object. The analytics server may receive a third image. The analytics server may also receive a request to identify one or more objects within the third image. The analytics server may execute the trained AI model to identify one or more objects within the third image received. In an example, the analytics server may receive a 4D CT scan image of a second patient. The analytics server may use the AI model (previously trained using 4D CT scan image of the first patient) to identify one or more objections (e.g., organs and/or tumor(s)) within the second patient's 4D CT scan. The analytics server may also use the methods 200 and/or 300 to further train the AI model using the second patient's image. Therefore, with each image received (or set of images), the analytics server further train the AI model. Consequently, the analytics server may iteratively/continuously improve the AI model.

The analytics server may use the same set of images to train the AI model and segment the objects. For instance, the analytics server may receive a 4D CT image of a patient along with an instruction to segment one or more objects within the received 4D CT scan. The analytics server may extract five images from the received 4D CT scan. The analytics server may train the AI model using the first two images and then apply the trained model to segment the following three images.

The "third image," as used herein may refer to any subsequent images received by the analytics server where the analytics server applies the trained AI model to segment the received image. Therefore, the "third image" may refer to a series of images (e.g., a second 4D CT scan of the same or different patient).

Figure 6:
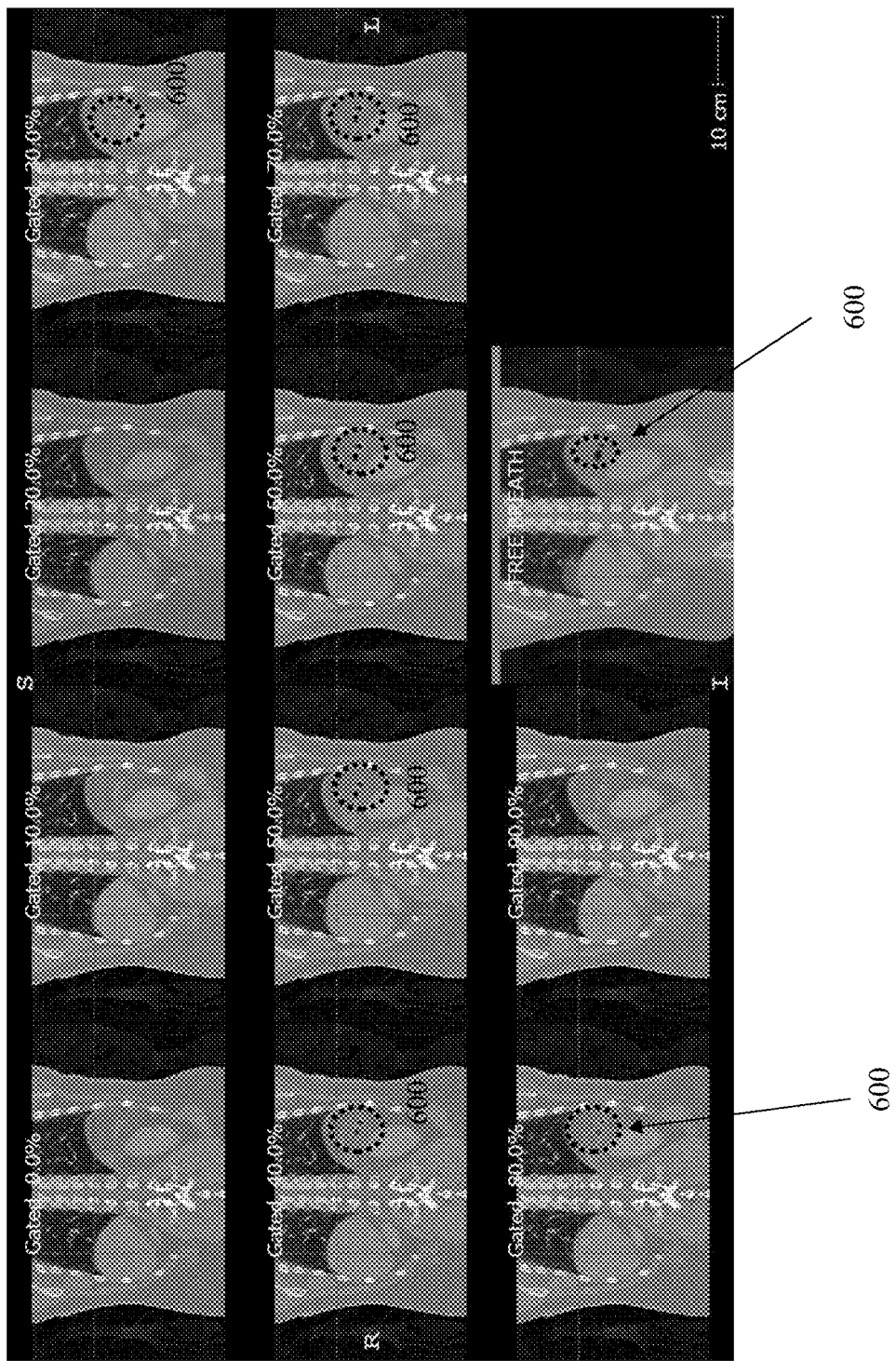
FIGS. 6-7 illustrate a temporal series of medical images, according to an embodiment.
Figure 8:
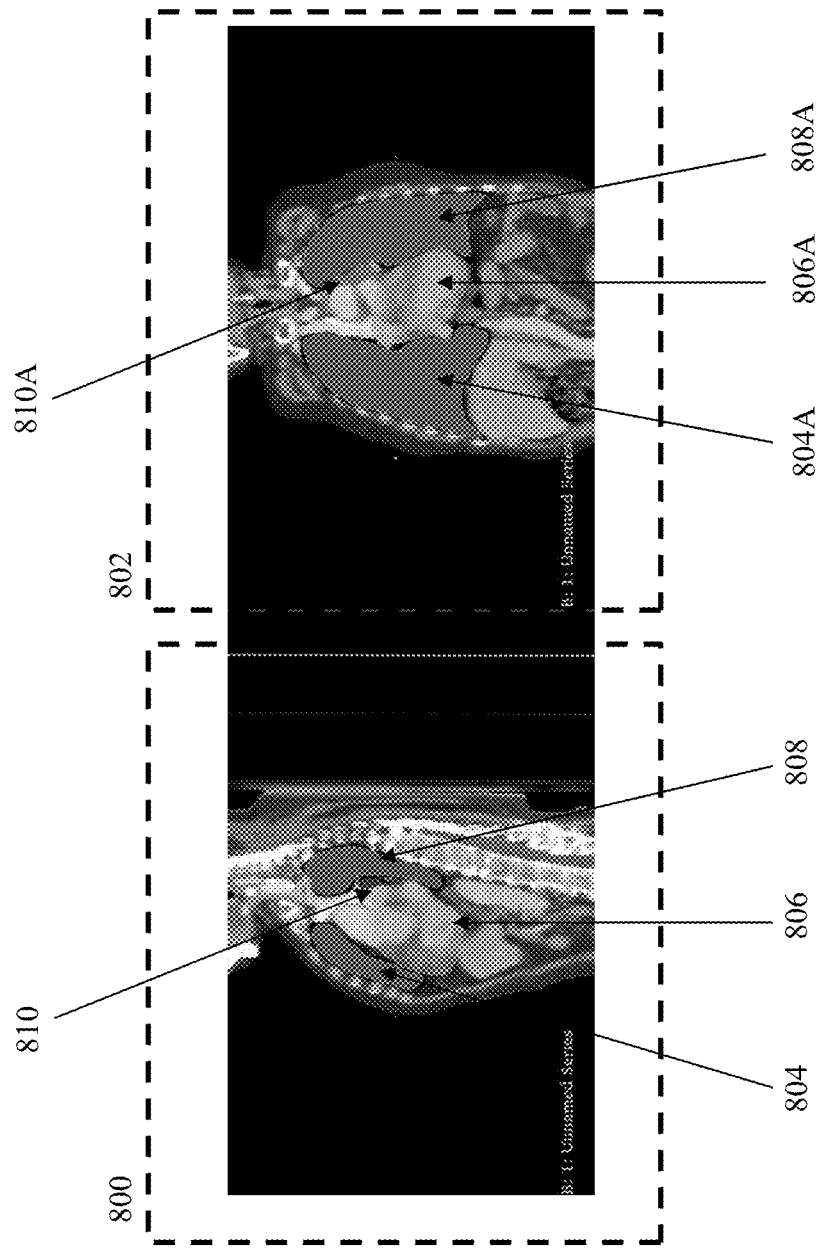
FIGS. 8-9 illustrate examples of displaying results of execution of the AI training system, according to an embodiment.

Referring now to FIG. 8, non-limiting examples for results of execution of AI models trained using the methods and systems described herein are provided. GUIs 800 and 802 represent different medical images produced for the same patient. The GUIs 800 and 802 are different renderings of the same object (tumor and/or other organs) for the same time period. Therefore, the GUIs are illustrating results of segmenting and contouring performed using the methods and systems described herein. For instance, GUI 800 may correspond to an image generated using any of the medical imaging techniques described herein and the GUI 802 may correspond to another image generated using any of the medical imaging techniques described herein illustrating the same patient from a different angle. In a non-limiting example, the patient (whose medical images are also depicted in FIG. 6) may be asked to breathe where a medical imaging device generates time-dependent images, as depicted in FIG. 8.

The analytics server may use the AI modeling techniques to identify one or more organs within the received images. For instance, the analytics server may execute an AI model that is trained using the methods and systems described herein. As a result, the analytics server identifies organs 804-808 and 804A-808A (and tumor 810 and 810A). The analytics server may displays the identified organs as visually distinct elements, such as by using different colors, different hatch patterns, or any contouring methods. In the depicted embodiment, the patient suffers from lung cancer and the analytics server identifies the patient's lungs (804 and 808) and the tumor 810. The analytics server then identifies the same organs and tumor using the methods and systems described herein (804A, 808A, 810A). Using the methods and systems described herein, the analytics server also identifies the patient's heart (806 and 806A).

Figure 9:
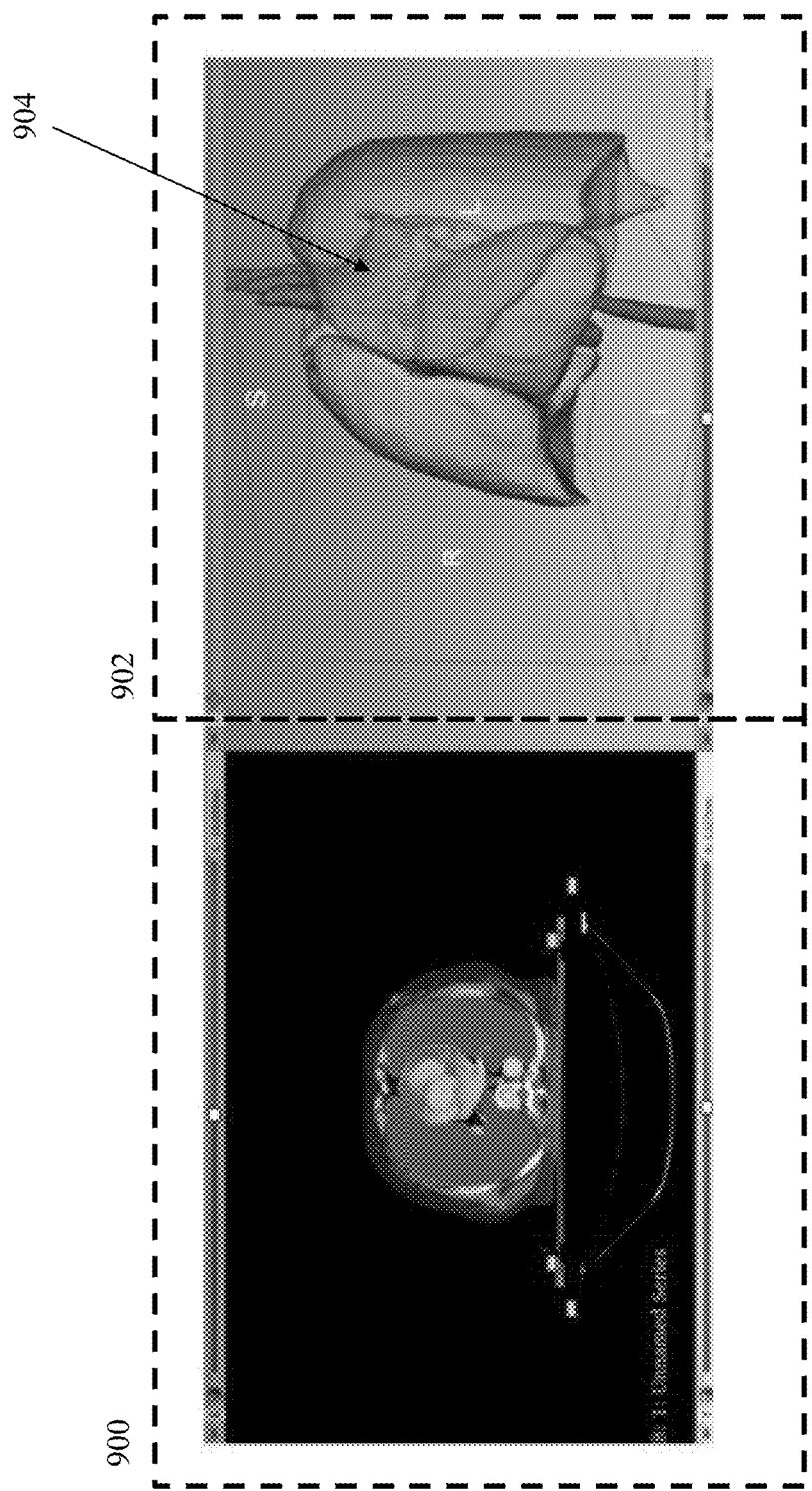

The analytics server may also displays two or three dimensional rendering of the same organs as illustrated in GUIs 900 and 902 of FIG. 9. For instance, tumor 904 is a rendering of the patient's tumor 810. Moreover, GUI 900 offers a cross sectional view of the same patient's lungs.

In some embodiments, the analytics server may use one or more frames extracted from a 4D CT scan image to train the AI model and use the trained AI model to analyze object within subsequent frames of the same 4D CT scan image.

For instance, the analytics server may receive a 4D CT scan image and may extract 10 frames (5-second increments). The analytics server may use the first three frames to train the AI model and then execute the trained model to identify objects within the next three frames.

The analytics server may analyze the set of images using the AI model and may display the results on an end user's computing device, such as the user computing devices 120, described in FIG. 1. For instance, the analytics server may display a 4D CT scan image where an additional image (layered in addition to the 4D CT scan image) identifies each organ.

Figure 3:
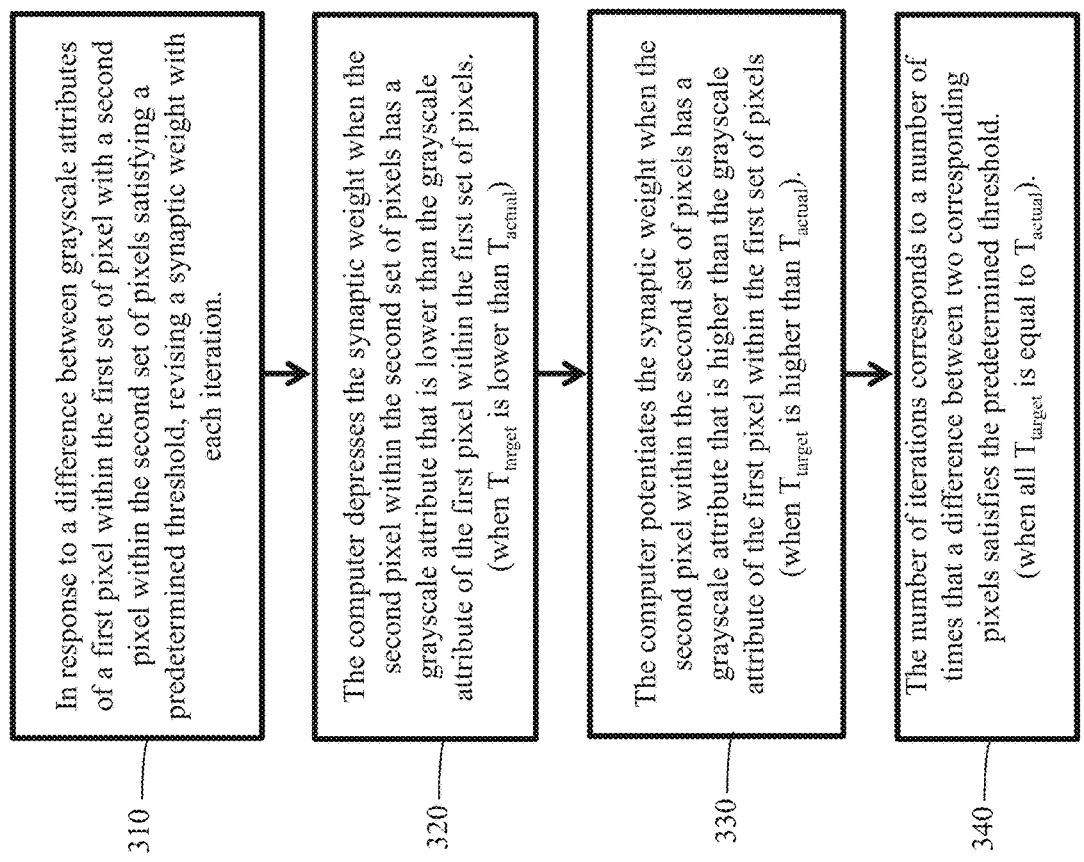
FIG. 3 illustrates a flow diagram of a process executed in an AI training system, according to an embodiment.

Referring now to FIG. 3, the method 300 illustrates a flow diagram of a process executed in an AI training system, according to an embodiment. The method 300 includes steps 310-340. However, other embodiments may include additional or alternative execution steps, or may omit one or more steps altogether. The method 300 is described as being executed by a server, similar to the analytics server described in FIG. 1B. However, one or more steps of method 300 may also be executed by any number of computing devices operating in the distributed computing system described in FIG. 1B. For instance, one or more user computing devices may locally perform part or all the steps described in FIG. 3.

At step 310, the analytics server may revise a synaptic weight associated with the first or the second pixel with each iteration, in response to a difference between grayscale attributes of a first pixel within the first set of pixel with a second pixel within the second set of pixels satisfying a predetermined threshold.

The neurons within the AI model used/trained by the analytics server may be of type Leaky-Integrate-&-Fire (LIF). These neurons may evolve using the following evolution equations:

$$\tau_m(dV_m/dt) = -(v_t - v_{rest}) + g_t \cdot W + J_b$$

Where: $v_m$=membrane potential
$v_{rest}$=resting potential of a neuron membrane that it slowly settles into.
$g_t$=synaptic conductance
$W$=synaptic connection matrix
$J_b$=bias current injected from other external sources
A neuron spikes when $v_m > V_{threshold}$ (some pre-defined threshold voltage).
And the conductance of synapse changes may be calculated according to the following:

$$g_{t+1} = g_t \cdot e^{-(\tau g)} + \delta_t$$

where $\tau_g$ is the time-constant for conductance decay, and $\delta_t=1$ if there is a pre-synaptic spike, else $\delta_t=0$.

Figure 4A:
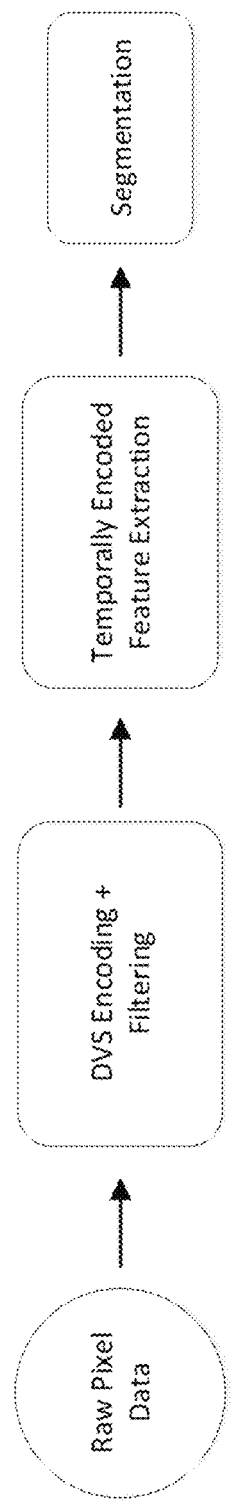
FIGS. 4A-B illustrate methods of training AI models, according to an embodiment.

Referring now to FIG. 4A, a schematic representation of the methods/systems described herein is presented, according to an embodiment. FIG. 4A illustrates an example process flow for 4D CT segmentation according to an embodiment. However, it is understood that this figure applies to training any AI model based on any imagery. As depicted, the analytics server may encode 4D CT data (e.g., using a dynamic vision sensor (DVS) based encoding scheme) to generate encoded data representing motion energy of the movements represented/illustrated in 4D CT data.

Figure 4B:
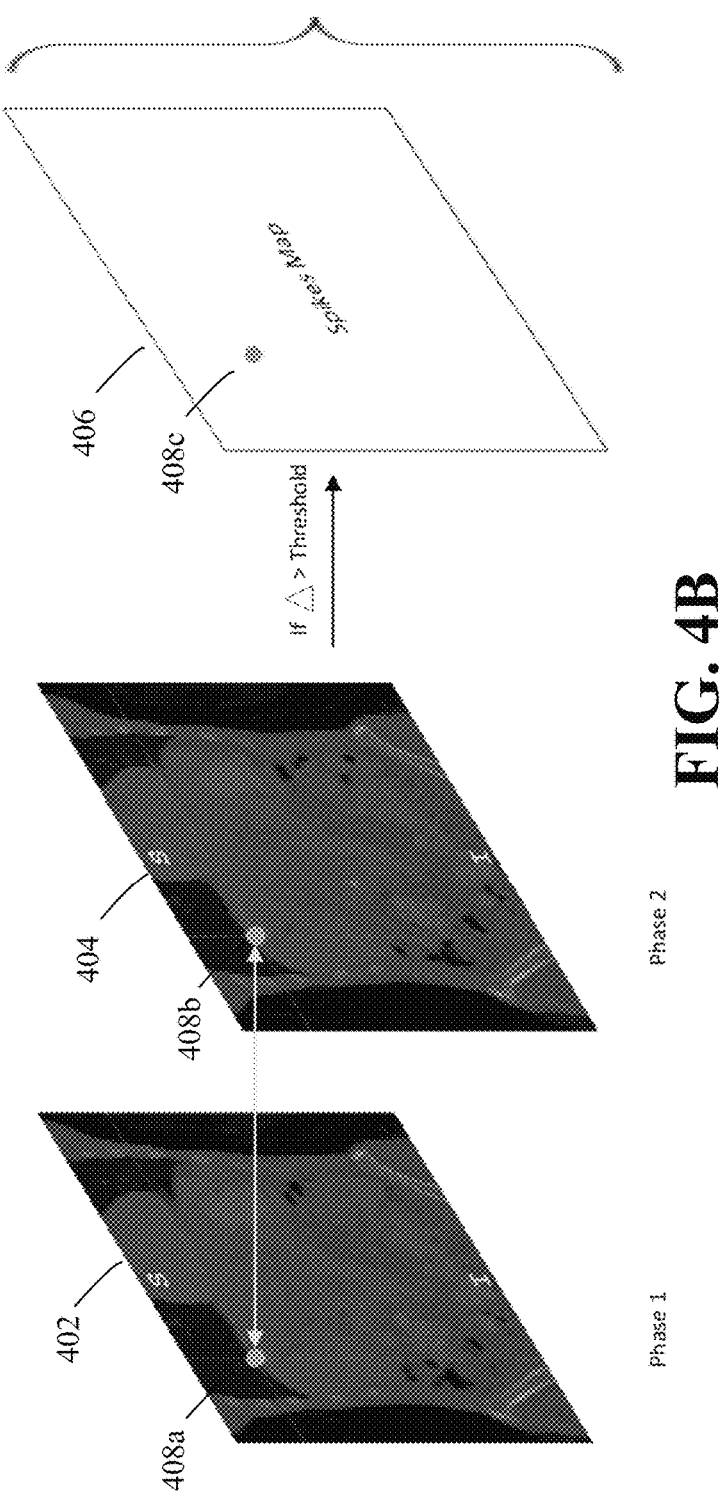

As described above, the analytics server may limit the training based on a pixel difference satisfying a predetermined threshold. For example, the training mythology may be triggered only when one or more pixels within an image is different from a previously analyzed image, as depicted in FIG. 4B. DVS encoding may generate a frame of encoded data, based on a difference between corresponding pixels in respective frames of the raw 4D CT data. The analytics server may then revise the synaptic weight used by the AI model in accordance with the encoded data. For instance, the AI model may ingest the encoded data where the analytics server causes the AI model to train itself using the encoded data.

In a non-limiting example, a pixel of the encoded data may be represented as a spike if a difference between two corresponding pixels of the raw 4D CT data (data corresponding to the 4D CT scan image before the analytics server revises the synaptic weights) is greater than some predetermined threshold. In some implementations, the encoded data may be weighted (e.g., based on amounts of differences between corresponding pixels) to increase detectability of small actions in the 4D CT sequence. The analytics server may set the synaptic weights (e.g. potentiate or depress the synaptic weights) based on the inverse distribution of motion amplitude, to capture the motion of different regions as equally as possible.

FIG. 4B depicts an example of DVS encoding, in accordance with an embodiment. For instance, for a given frame of encoded data, a pixel of the frame represents a difference between two corresponding pixels each in a different respective frame of the raw 4D CT data. Pixels of the encoded frame are represented as input spike signals and ingested by the neural network (the AI model).

In the depicted embodiment, the analytics server receives a 4D CT image of a patient. The analytics server extracts two frames (e.g., different phases) from the received 4D CT image (frames 402 and 404). The analytics server may compare visual attributes of each pixels within the frames 402 and 404 and may compare the corresponding pixels. When the difference of pixel 408a and 408b satisfies a threshold (e.g., predetermined and revisable by the end user or a system administrator), the analytics server may revise the synaptic weights associated with the pixel 408a/b (depicted as pixel 408c). The methods/systems described in this figure (and other figures) applies to both two dimensional and three-dimensional images.

Referring back to FIG. 3, at steps 320-330, the analytics server may either depress or potentiate synaptic weights associated with the pixels. Specifically, at step 320, the analytics server may depress the synaptic weight when the second pixel within the second set of pixels has a grayscale attribute that is lower than the grayscale attribute of the first pixel within the first set of pixels. Moreover, at step 330, the analytics server may potentiate the synaptic weight when the second pixel within the second set of pixels has a grayscale attribute that is higher than the grayscale attribute of the first pixel within the first set of pixels.

The analytics server may apply additional filtering and/or weighting of the encoded 4D CT data before the AI model processes the image. More particularly, a frame of encoded data may include sub-portions (sub-frames), which are analyzed independently by the analytics server. The inclusion of a given sub-frame, or the relative synaptic weight of one sub-frame with respect to that of another sub-frame, may be based on one or more criteria, for example, based on whether a given sub-frame represents a motion energy, which satisfies a threshold. Additionally or alternatively, the analytics server may apply a pre-morphologic algorithm to extract the border or target sub-portions. For instance, the analytics server may provide encoded 4D CT data to the AI model to train the AI model (e.g., frames of encoded reference 4D CT data are inputted as spike sequences to a sparsely connected random neural network).

Figure 5A:
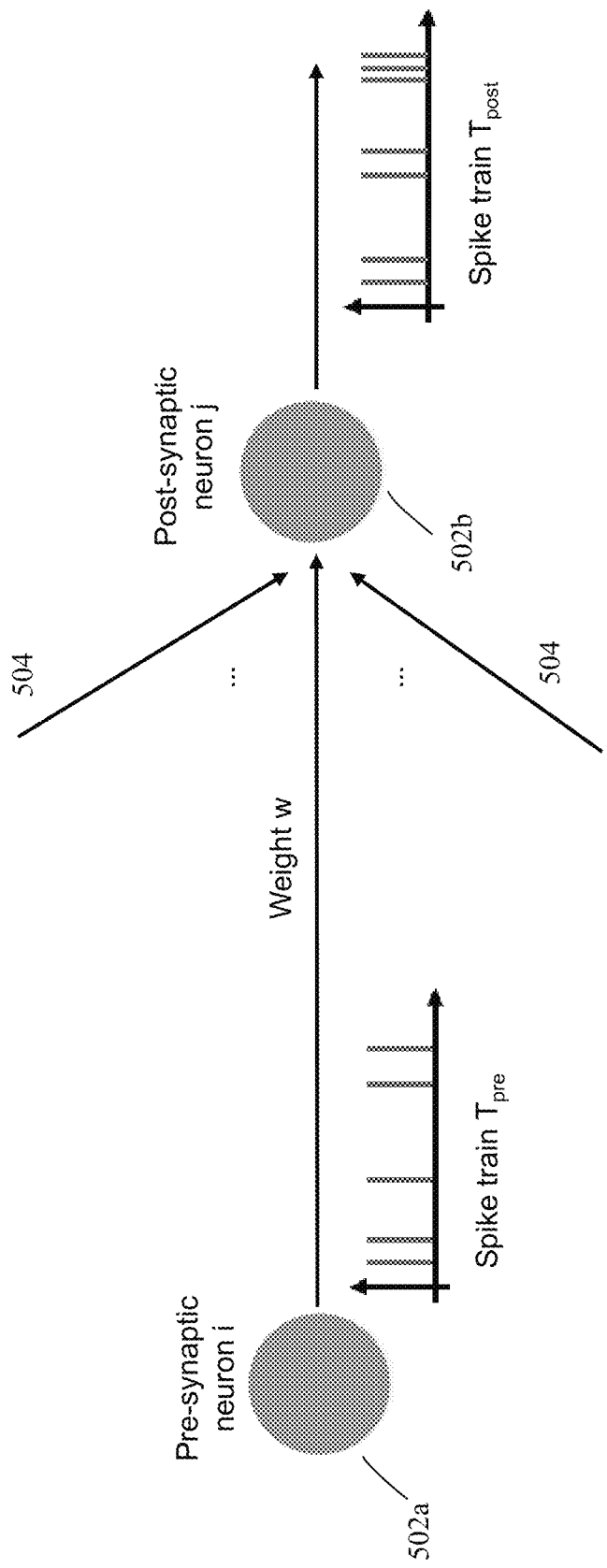
FIGS. 5A-B illustrate methods of training AI models, according to an embodiment.
Figure 5B:
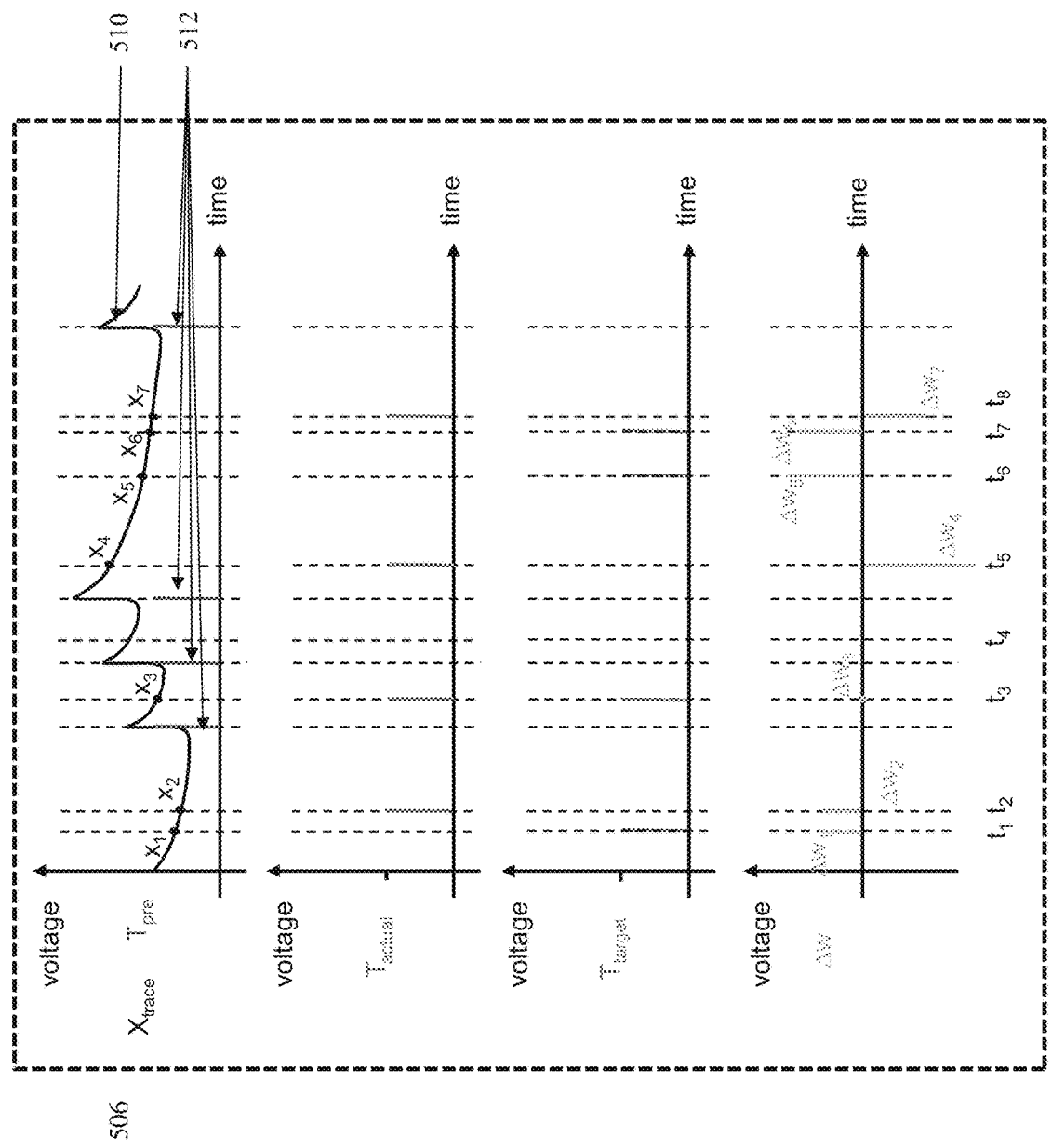

FIGS. 5A-B visually illustrate signaling performed during training of the AI model (e.g., supervised learning). More specifically, these figures visually depict how synaptic weights can be revised (e.g., depressed or potentiated) by the analytics server. The analytics server may compare different images (or different frames of a moving image, such as 4D CT) to determine whether/how synapse weights are to be changed.

As described above, the AI model may utilize a neural network. The neural network may include a series of interconnected nodes that correspond to visual attributes of the images received where the AI model uses the attribute (represented by the series of nodes or neurons) to identify/predict various objects within received images. While a portion (e.g., subset) of the nodes within the set of nodes are input nodes corresponding to the pixels within the images, another portion of nodes within the set of nodes may correspond to a likelihood of each respective pixel corresponding to at least one object. For instance, a subset of the nodes may correspond to an attribute of each pixel (e.g., input nodes). A second set of nodes may correspond to a likelihood that the pixels (represented by the input nodes) belong to a particular object depicted within an image, such as a tumor. The neural network may use these interconnected nodes to identify and segment different objects depicted in one or more images.

As depicted in FIG. 5A, the neural network utilized by the AI model, may include node 502a (Pre) that may output spike signaling to another node 502b. These nodes are also designated as Pre and Post because node 502a (Pre) is connected to the node 502b (Post). The Pre node may transmit/output spikes to the post node. The analytics server may train the AI model by revising the weights associated with the pre and post nodes. As depicted by lines 504, the post node may also be connected to other nodes as well.

The analytics server may train the AI model by calculating the magnitude of any change ($\Delta w$) to be applied to the synaptic weights (W). Therefore, this figure visually illustrates an example of how the analytics server determines the $\Delta w$ that is to be applied to the synaptic weight (W) of a synapse/node between any Pre node and a Post node. As depicted, the analytics server may revise node weights, which may correspond to the weight of different nodes within the AI model that define the graphical/visual attributes of the images received, such that $T_{actual}$ is eventually equal to $T_{target}$.

The value of $\Delta w$ may be a function of both a trace voltage ($X_{trace}$) from the pre node to the Post node and a difference between an actual output ($T_{actual}$) from the Post node and an ideal target output ($T_{target}$) from the Post node. The $X_{trace}$ may represent the pre-neuronal spiking history and/or the actual trace voltage for the post node. The analytics server may calculate the $X_{trace}$ via actual measure (e.g., if it is running on a neuromorphic hardware) or simulation using leaky integrate and fire (LIF) neuron model techniques. The $T_{target}$ may represent the ground truth-value, which may be acquired via manual labeling or annotation. In some configurations, the ground truth may also be inputted by a third-party data source, such as by importing the training data.

For example, in the timing diagram 506, the lines above the horizontal line ($T_{pre}$ or lines 512) represent data spikes of the pre-synaptic neuron, which are identified by the analytics server (e.g., sent by the Pre node to the Post node).

These data spikes may correspond to visual differences between corresponding pixels. The pre-synaptic "trace" voltage ($X_{trace}$ that are represented by lines 510) models the pre-neuronal spiking history. Every time a pre-synaptic neuron outputs a result (e.g., "fires"), $X_{trace}$ may increase by 1, otherwise it may decay exponentially.

After a spike, $X_{trace}$ may decay over time until a next spike by $T_{pre}$ is detected. The amount of change $\Delta w$ may be based on a current level of $X_{trace}$, and further based on a difference between (1) an actual spike signal output $T_{actual}$ from the Post node (where $T_{actual}$ is in comparison to $T_{pre}$), and/or (2) a target output $T_{target}$ that the Post node should output in response to $T_{pre}$. As depicted, $T_{target}$ may represent the contribution by the Post node to a desired neural network output, which, for example, has been assigned a priori as that which is to represent a particular activity. The analytics server may calculate the $\Delta w$ value by calculating a difference $[T_{target}-T_{actual}]$, which is weighted by the current value of $X_{trace}$. For example, as depicted in FIG. 5B:

For time point $t_1$, $\Delta w_1 = X_{trace}(T_{target}-T_{actual}) = x_1(1-0)$
$= x_1$ For time point $t_2$, $\Delta w_2 = X_{trace}(T_{target}-T_{actual}) = x_2(0-1)$
$= -x_2$ For time point $t_3$, $\Delta w_3 = X_{trace}(T_{target}-T_{actual}) = x_3(1-1)$
$= 0$ For time point $t_4$, $\Delta w_4 = X_{trace}(T_{target}-T_{actual}) = x_4(0-1)$
$= -x_4$ For time point $t_5$, $\Delta w_5 = X_{trace}(T_{target}-T_{actual}) = x_5(1-0)$
$= x_5$ For time point $t_6$, $\Delta w_6 = X_{trace}(T_{target}-T_{actual}) = x_6(1-0)$
$= x_6$ For time point $t_7$, $\Delta w_7 = X_{trace}(T_{target}-T_{actual}) = x_7(0-1)$
$= -x_7$ The disclosed training approach may implement a spiked-timing dependent plasticity (STDP) behavior of neurons. The analytics server may be adapted to accommodate the training of a neural network to produce a desired priori output. After such training, 4D CT segmentation can be performed. For instance, the analytic server may train the AI model in accordance with the revisions discussed herein. When the trained AI model ingests a new image (or a series of frames/images), the AI model can utilize the revised weights to contour/segment different objects within the received images. The disclosed framework implements a method similar to human brain activity where neurons generate action potentials (e.g., fixed voltage pulses), the timing of which is used to represent signal content. The framework described herein and performed by the analytics server encodes 4D CT data, which shows the performance of an organ movement where the type of encoding disclosed herein enables a spike-based neural network to efficiently segment the images, based on time-relevant information.

At step 340, the analytics server may iteratively repeat the method 300 where the number of iterations corresponds to a number of times that a difference between two corresponding pixels satisfies the predetermined threshold. As discussed herein, the analytics server may continuously train the AI model using the methods and systems described herein. The number of iterations (e.g., the number of times that the analytics server trains the AI model) may correspond to the number of frames and/or the number of times that a difference in pixel attributes are identified. For instance, the analytics server may iteratively train the model each time $T_{target}$ and or $T_{actual}$ values need to be adjusted. Therefore, the number of iterations may depend on $T_{target}$ and $T_{actual}$ values. When $T_{target}=T_{actual}$, the analytics server may cease training the neural network.

In a non-limiting example, the analytics server receives five images. The analytics server may analyze the first image using an AI model to identify one or more objects within the received image. The AI model may be pre-trained using a variety of methods including the methods and system described herein or any other conventional training methods. If the AI model is pre-trained, the analytics server may use the methods and systems described herein to further train the AI model in order to achieve better results.

The AI model may then analyze pixels within the second image and may identify corresponding pixels, which have visually changed (more than a predetermined threshold) compared to their corresponding pixels within the first image. As a result, the analytics server may train the AI model using the methods and systems described herein. The analytics server may then analyze the third image and compare its pixels to the second image. As a result, the analytics server may re-train the AI model again using pixel differences within the third image and the second image. The analytics server may continue this iterative process until is the last image is analyzed. Therefore, the analytics server may iteratively train the AI model five times (or fewer).

In another non-limiting example, the analytics server may train the AI model using a single 4D CT image, depicted in FIG. 6. As depicted, FIG. 6 includes a various frames extracted from a 4D CT image corresponding to a patient's respiration cycle. In this non-limiting example, the patient is asked to breathe and the 4D CT image is generated from a full breath cycle (e.g., starting from the image gated at 0% and continuing to the image gated at 90%. The analytics server may extract 10 images from the received 4D CT. The first five phases indicate the motion from the end of inhalation (EOI) to the end of the exhalation (EOE). As depicted, the patient whose medical imaging is illustrated in FIG. 6 suffers from a lung tumor 600, which can be identified using the methods and systems described herein. As depicted, the tumor 600 is not visible in every image. Therefore, to identify the tumor 600, the analytics server uses time-dependent images.

Figure 7:
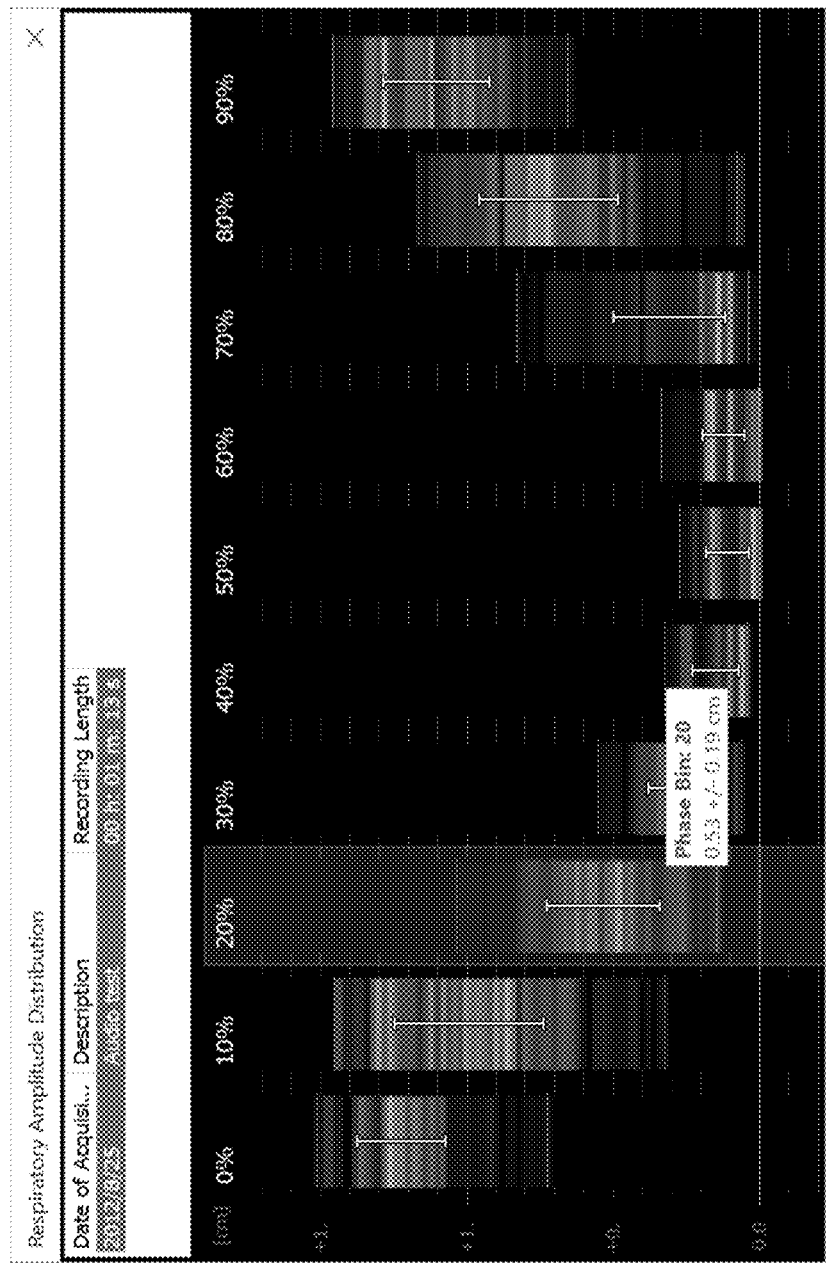

The number of images extracted may correspond to a predetermined range (e.g., respiratory amplitude). For instance, as depicted in FIG. 7, the patient's breath has lasted 1 minute and 13 seconds and the analytics server extracts and image corresponding to each 10% breath increments in addition to an image before the patient starts breathing and another image when the patient exhales (total of 10 images). The end user may revise these increments. For instance in other embodiments, the analytics server may extract 22 images (e.g., 5% increments). The analytics server may analyze the images extracted and utilize the methods/systems described herein to iteratively train the AI model.

The analytics server may analyze each frame and train the AI model accordingly, such that the AI model can be trained based on the patient's own images. The training model described herein allows the analytics server to use fewer images to train the model. Furthermore, because the AI model is trained using the patient's own images, the AI model may produce more accurate results (e.g., when compared to other AI models trained on other patient's images/data).

The training methods/systems described herein apply to all SNN applicable encoding methods. The non-limiting embodiments described herein use DVS encoding. However, it is expressly understood that the methods/systems described herein can apply to other encoding methods, such as the difference of Gaussians (DoG) method. In the DoG method, the analytics server may detect contrasts in the inputted image and may encode the strength of these contrasts in the latencies of its output spikes (e.g., the higher the contrast, the shorter the latency). The analytics server may then train the AI model according to the methods and systems described herein.

The analytics server may also train the AI model using rank-order coding methods. For instance, the analytics server may use this method separately, (e.g. to handle static images) or as a complementary encoding method to other methods described herein to capture all the necessary anatomic structure information. Therefore, encoding methods and systems to revise synaptic weights are not limited to only one method. For instance, the analytics server may use a combination of methods to train the AI model.

The analytics server may also use various user interactions to further train the AI model. For instance, the analytics server may monitor the electronic device displaying the results generated via executing the trained AI model to identify interactions between the end user and the electronic device while the electronic device is outputting the results. When the analytics server outputs the predicted results onto one or more user electronic devices, the analytics server may monitor the user's interactions with the results. As will be described below, the analytics server may then train the AI model based on the monitored data.

When the end user performs an activity on the electronic platform, the analytics server may track and record details of the end user's activity. For instance, when a predicted result is displayed on the user electronic device, the analytics server may monitor to identify whether the end user has interacted with the predicted results by editing, deleting, accepting, or revising the results. The analytics server may also identify a timestamp of each interaction, such that the analytics server records the frequency of modification, duration of revision/correction.

The analytics server may utilize an application programming interface (API) to monitor the end user's activities. The analytics server may use an executable file to monitor the user's electronic device. The analytics server may also monitor the electronic platform displayed on an electronic device via a browser extension executing on the electronic device. The analytics server may monitor multiple electronic devices and various applications executing on the electronic devices. The analytics server may communicate with various electronic devices and monitor the communications between the electronic devices and the various servers executing applications on the electronic devices.

In some embodiments, the analytics server may monitor the data packages received and sent by each electronic device to monitor the content of what is displayed/executed/modified on the electronic device. The communication may take any suitable form. For example, the electronic device may execute an application (e.g., browser extension) having an executable file that enables a user to navigate to the electronic platform (e.g., web site).

The analytics server may use several techniques to track user's activities on the electronic device, such as by tracking browser cookies and/or screen-scraping protocols. In another example, the analytics server may track the user activity by periodically retrieving user's web browser cookies. The analytics server may transmit cookies to a system database where they can be analyzed (e.g., in batches) to identify user activities.

In some configurations, the analytics server may monitor the electronic device using an executable file (application) installed as a browser extension. The browser extension (executable file) may be executing as a background process of the electronic device. For instance, the browser extension may be transparent to the user operating the electronic device. In this way, the analytics server is able to monitor the user's activities without disturbing the user and/or obfuscating the display screen of the electronic device. In some embodiments, the analytics server may activate a monitoring module (e.g., browser extension or executable file) upon outputting the results on the electronic platform. The analytics server may use the data collected/monitored to train the AI model and improve its predicted results.

The analytics server may display a prompt requesting the users to provide feedback regarding the predicted results outputted by the analytics server. For instance, the analytics server may display a prompt having an input element (e.g., text string input, drop down menu, radio button). The end user may interact with the prompt to input a feedback regarding the accuracy of the results outputted by the analytics server.

The feedback provided by the users may be a binary and/or a numerical input. For instance, the analytics server may provide a simple "thumb up/thumbs down" prompt where the user can rate the accuracy of the results using a binary scale. In some embodiments, the analytics server may request the user to input a number within a predetermined scale that represents the accuracy of the results (e.g., 0-10 scale). The analytics server may then collect the feedback data and generate the second set of training data accordingly.

The analytics server displays the prompts on the electronic user devices based on various predetermined rules and criteria. For instance, in some embodiments, the analytics server may always display a prompt requesting users' feedback. In some embodiments, the analytics server may display the prompt based on a predetermined frequency (e.g., 50% of instances where a predicted result is displayed). Furthermore, the analytics server may select the users receiving the prompt based on predetermined rules. For instance, the analytics server may select the users randomly. In some configurations, the predetermined rules may require the analytics server to display the prompt for users who satisfy a certain threshold (e.g., only for users who have three or more years of experience).

In some configurations, the analytics server only displays the prompt when the displayed predicted results satisfy a threshold. For instance, the analytics server may only display the prompt when the results correspond to AI-enabled image processing or only when the end user revises a predicted result. A system administrator can modify all the predetermined rules and threshold. The system administrator can also customize the predetermined rules and thresholds, such that the analytics server displays the prompts to a customized set of users for a customized set of results. For instance, a predetermined set of rules may require the analytics server to display the prompt asking a thumbs up/thumbs down feedback for doctors with more than two years of experience when the results corresponds to cancer diagnosis.

In some embodiments, the analytics server may periodically train the AI model. For instance, the analytics server may collect/monitor user interactions and store the corresponding data. The analytics server may then use a predetermined frequency (e.g., once a month or once a week) to train the AI model using the stored training datasets. A system administrator can modify the frequency of the batch training.

The analytics server may have other "triggering" conditions to train the AI model. For instance, the analytics server may continuously compare the results of execution of the AI model with a ground truth. The analytics server may then train the AI model using the training datasets when the analytics server determines that the results generated by the AI model are incorrect or satisfy a threshold with respect to the ground truth. In a non-limiting example, the analytics server may train the AI model when the analytics server identifies that the results generated by the AI model are incorrect by a predetermined threshold (e.g., at least 8% difference between a ground truth and the results generated by the AI model).

The analytics server may implement safeguards to ensure that training the AI model is conducted in an acceptable manner. As discussed above, the analytics server may generate the training datasets based on predefined criteria to ensure that the models are trained based on feedback received from users that satisfy certain criteria (e.g., more credible/experienced users). In another example, the analytics server may implement a manual review where a system administrator may review the feedback data. The analytics server may display a prompt onto one or more system administrator's computers and request the system administrators to review the feedback data before the feedback data is included in the training datasets.

The analytics server may train the AI model when the AI model produces results that receive feedback that satisfies a threshold. For instance, the analytics server trains the AI model when the results outputted on the electronic platform receive a feedback (e.g., thumbs down or modification/revision of the results by the users) more frequently than a predefined threshold (e.g., 40% of time).

The analytics server may train the model based on a customized (predetermined) segmentation of training data and/or users. For instance, the analytics server may segment the training data before training the AI model. The analytics server may train the AI model in a customized and segmented manner that is meaningfully tethered to the end users' needs. In a non-limiting example, the analytics server may train the AI model based on feedback received from a selection of users (e.g., users who work at a particular clinic or users who satisfy a certain score). As a result, the analytics server may customize the AI model for a particular clinic. This training method allows the AI model to adapt to the particular clinic and produce results that are more acceptable to the users within that clinic.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Figure 10:
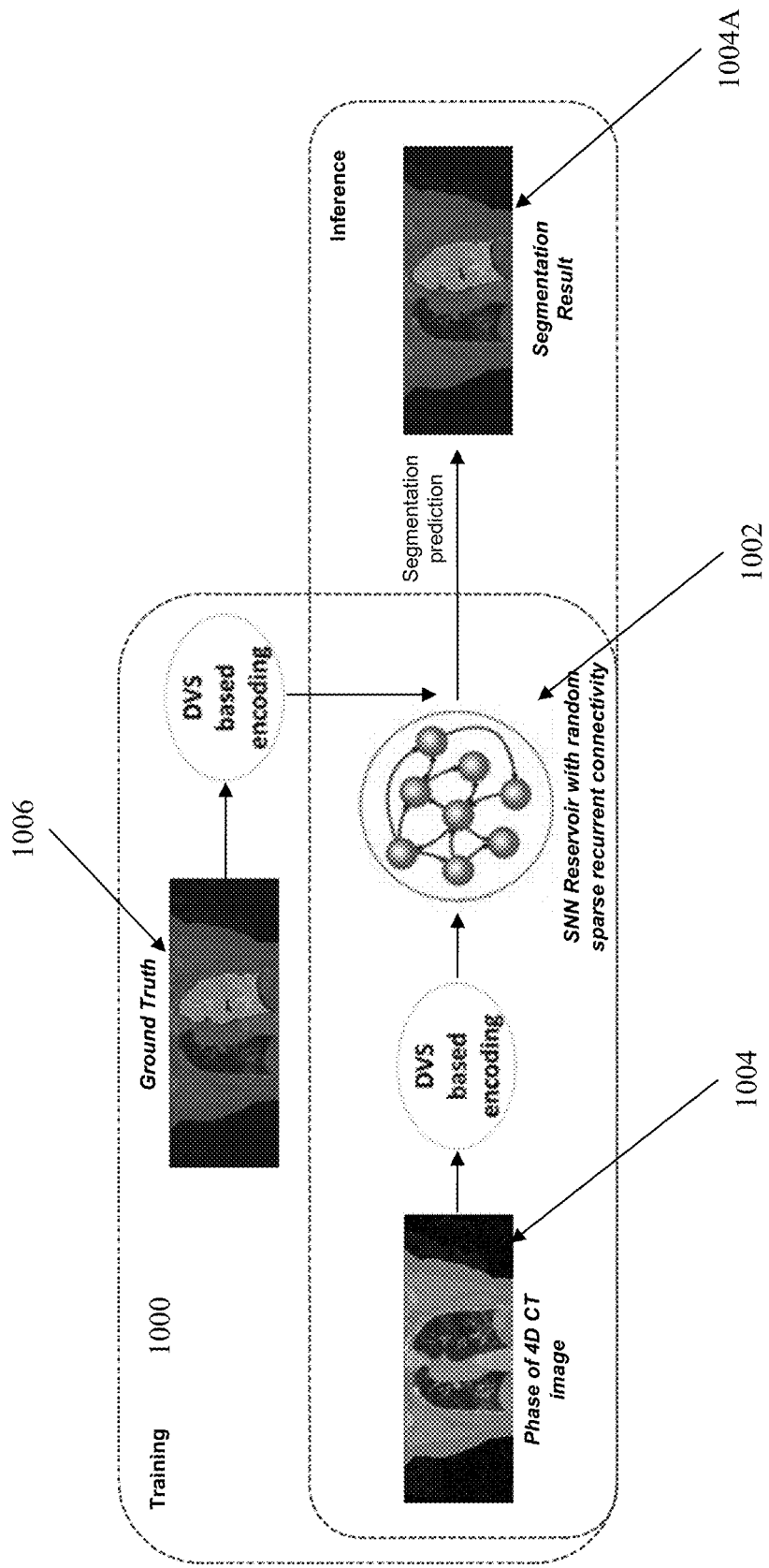
FIG. 10 illustrates an AI training system disclosed herein, according to an embodiment.

Referring now to FIG. 10, a non-limiting example of the methods and systems described herein is visualized. The training system 1000 trains the AI model 1002, such that when the AI model 1002 receives the image(s) 1004, the AI model is able to segment different objects (e.g., tumors) within the image(s) 1004. The training system may include two separate training parts. The training may include ingesting ground truth data 1006 to train the AI model 1002 using various training methods. Ground truth data 1006 may include images (e.g., CT scan or 4D CT scan images) of known objects (e.g., tumors). The AI model 1002 may ingest the ground truth data to train itself.

In conjunction with training the AI model 1002 using ground truth data, the analytics server may also train the AI model 1002 using the DVS-based encoding described herein (e.g., FIGS. 2 and 3). For instance, the AI model 1002 may be trained using different phases of 4D CT scan image of a patient (e.g., the same image being segmented by the analytics server). Therefore, the methods and systems described herein can be used in conjunction with conventional ground truth ingestion methods. Moreover, the AI model 1002 may be trained using the image(s) being analyzed (e.g., segmented) themselves. The AI model 1002 then segments the image(s) 1004 and displays the segmented results (1004A).

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

I claim:

1. A method comprising:
executing, by a computer, an artificial intelligence model utilizing a spiking neural network to segment one or more objects represented by a first set of pixels in a first image, the spiking neural network comprising a set of nodes corresponding to the first set of pixels, each node having a synaptic weight, wherein at least a first portion of nodes within the set of nodes represents input nodes corresponding to the first set of pixels and a second portion of the nodes within the set of nodes represents output nodes associated with a likelihood of each respective pixel corresponding to at least one object within the one or more objects;
comparing, by the computer, a grayscale attribute of each pixel within the first set of pixels with a corresponding pixel within a second set of pixels of a second image of the one or more objects;
iteratively training, by the computer using a supervised spiked-timing dependent plasticity method, the spiking neural network by:
in response to a difference between grayscale attributes of a first pixel within the first set of pixels with a second pixel within the second set of pixels satisfying a predetermined threshold:
a node corresponding to the first pixel transmits a spike, and
revising a synaptic weight associated with the first or the second pixel with each iteration; and
upon receiving a third image, executing, by the computer, the artificial intelligence model utilizing a trained spiking neural network to segment the one or more objects in the third image.

2. The method of claim 1, wherein the computer revises the synaptic weight using the following formula:

$$\Delta w = X_{trace}(T_{target} - T_{actual})$$

wherein $\Delta w$ represents a required weight change, wherein $X_{trace}$ represents a trace voltage from pre-node for post-node, wherein $T_{target}$ represents a ground truth value, and wherein $T_{actual}$ represents an actual spike output during training.

3. The method of claim 2, wherein the computer depresses the synaptic weight when $T_{target}$ is lower than $T_{actual}$.

4. The method of claim 2, wherein the computer potentiates the synaptic weight when the $T_{target}$ is bigger than $T_{actual}$.

5. The method of claim 1, wherein the computer extracts at least one of the first image or the second image from a media element.

6. The method of claim 5, wherein the media element is a four-dimensional computed tomography (CT) scan image.

7. The method of claim 6, wherein the computer extract the at least one of the first image or the second image from the media element based on a predetermined time period.

8. The method of claim 7, wherein the predetermined time period is received and revisable by a user operating a computing device that displays results of execution of the artificial intelligence model.

9. The method of claim 5, wherein the third image is extracted from the media element.

10. The method of claim 1, wherein the third image represents a neighboring phase of a four dimensional CT scan image.

11. A system comprising:
a server comprising a processor and a non-transitory computer-readable medium containing instructions that when executed by the processor causes the processor to perform operations comprising:
execute an artificial intelligence model utilizing a spiking neural network to segment one or more objects represented by a first set of pixels in a first three-dimensional image, the spiking neural network comprising a set of nodes corresponding to the first set of pixels, each node having a synaptic weight, wherein at least a first portion of nodes within the set of nodes represents input nodes corresponding to the first set of pixels and a second portion of the nodes within the set of nodes corresponds to a likelihood of each respective pixel corresponding to at least one object within the one or more objects;
compare a grayscale attribute of each pixel within the first set of pixels with a corresponding pixel within a second set of pixels of a second image of the one or more objects;
iteratively train using a supervised spiked-timing dependent plasticity method, the spiking neural network by:
in response to a difference between grayscale attributes of a first pixel within the first set of pixels with a second pixel within the second set of pixels satisfying a predetermined threshold:
a node corresponding to the first pixel transmits a spike having a synaptic weight, and
revising the synaptic weight associated with the first or the second pixel with each iteration; and
upon receiving a third image, execute the artificial intelligence model utilizing a trained spiking neural network to identify the one or more objects in the third image.

12. The system of claim 11, wherein the server revises the synaptic weight using the following formula:

$$\Delta w = X_{trace}(T_{target} - T_{actual})$$

wherein $\Delta w$ represents a required weight change, wherein $X_{trace}$ represents a trace voltage from pre-node for post-node, wherein $T_{target}$ represents a ground truth value, and wherein $T_{actual}$ represents an actual spike output during training.

13. The system of claim 11, wherein the server depresses the synaptic weight when $T_{target}$ is lower than $T_{actual}$.

14. The system of claim 11, wherein the server potentiates the synaptic weight when the $T_{target}$ is bigger than $T_{actual}$.

15. The system of claim 11, wherein the server extract at least one of the first image or the second image from a media element.

16. The system of claim 15, wherein the media element is a four-dimensional computed tomography (CT) scan image.

17. The system of claim 16, wherein the server extract the at least one of the first image or the second image from the media element based on a predetermined time period.

18. The system of claim 17, wherein the predetermined time period is received and revisable by a user operating a computing device that displays results of execution of the artificial intelligence model.

19. The system of claim 15, wherein the third image is extracted from the media element.

20. The system of claim 11, wherein the third image represents a neighboring phase of a four dimensional CT scan image.

* * * * *